(12) United States Patent
Kroll et al.

(10) Patent No.: US 6,287,306 B1
(45) Date of Patent: Sep. 11, 2001

(54) EVEN TEMPERATURE LINEAR LESION ABLATION CATHETER

(75) Inventors: Mark W. Kroll, Orono; John D. Ockuly, Robbinsdale, both of MN (US); Rajesh Pendakanti, Sunnyvale, CA (US)

(73) Assignee: Daig Corporation, Minnetonka, MN (US)

( * ) Notice: Subject to any disclaimer, the term of this patent is extended or adjusted under 35 U.S.C. 154(b) by 0 days.

(21) Appl. No.: 09/276,210

(22) Filed: Mar. 25, 1999

Related U.S. Application Data
(60) Provisional application No. 60/090,209, filed on Jun. 22, 1998.

(51) Int. Cl.$^7$ .................................................. A61B 18/18
(52) U.S. Cl. ............................... 606/41; 606/42; 607/99; 607/101
(58) Field of Search .................................. 606/32, 34, 40, 606/41, 42, 45, 49; 604/21, 114; 607/96, 98–102

(56) References Cited

U.S. PATENT DOCUMENTS

| | | |
|---|---|---|
| 5,265,623 | 11/1993 | Kroll et al. . |
| 5,293,868 | 3/1994 | Nardella . |
| 5,487,385 | 1/1996 | Avitall . |
| 5,582,609 | 12/1996 | Swanson et al. . |
| 5,680,860 | 10/1997 | Imran . |
| 5,697,909 * | 12/1997 | Eggers et al. ........................ 604/114 |
| 5,720,775 | 2/1998 | Larnard . |
| 5,730,127 | 3/1998 | Avitall . |
| 5,843,075 * | 12/1998 | Taylor .................................... 606/34 |
| 5,954,719 * | 9/1999 | Chen et al. ............................. 606/42 |
| 5,971,983 * | 10/1999 | Lesh ....................................... 606/41 |
| 6,059,778 * | 5/2000 | Sherman ................................. 606/34 |
| 6,066,134 * | 5/2000 | Eggers et al. ........................... 606/32 |
| 6,076,012 * | 6/2000 | Swanson et al. ....................... 604/21 |

OTHER PUBLICATIONS

Blouin, L.T. and Marcus, F.I., "The Effect of Electrode Design on the Efficiency of Delivery of Radiofrequency Energy to cardiac Tissue In Vitro", *PACE,* vol. 12, pp 136–143, Jan., 1989, Part II.

Pendekanti, R. and Henriquez, C.S., "Spatial Potential and Current Distributions Along Transvenous Defibrillation Electrodes: Variation of Electrode Characteristics", *Annals of Biomedical Engineering,* vol. 24. pp. 156–167, 1996.

Nath, et al., "Basic Aspects of Radiofrequency Catheter Ablation", *Journal of Cardiovascular Electrophysiology,* vol. 5, No. 10, Oct. 1994.

* cited by examiner

*Primary Examiner*—Roy Gibson
(74) *Attorney, Agent, or Firm*—Scott R. Cox

(57) ABSTRACT

A linear lesion ablation catheter includes a conductive ablating portion having a predetermined resistivity profile for ablating tissue in a generally even temperature profile. In one embodiment, the conductive ablating portion is disposed on a distal portion of an elongate flexible member and has a resistance that increases exponentially along its length from a center of the ablating portion to a non-infinite value at opposite ends of the ablating portion. The ablating portion is adapted to produce a generally even temperature profile along a length of its surface when the ablating portion is in contact with a target tissue within a patient's body. In one example, the conductive ablating portion comprises a plurality of electrically connected conductive regions which extend from the center to the opposite ends of the ablating portion. Each of the conductive regions has a resistance value wherein the resistance values increase from section to section in successive orders of magnitude from the center of the ablating portion to the opposite ends of the ablating portion exponentially up to a non-infinite value. This predetermined resistivity profile produces linear lesions on target tissue without the resulting "edge effects" or "hot spots" at the ends of the electrode common in prior art linear lesion ablation catheters.

40 Claims, 9 Drawing Sheets

Distance from center of electrode

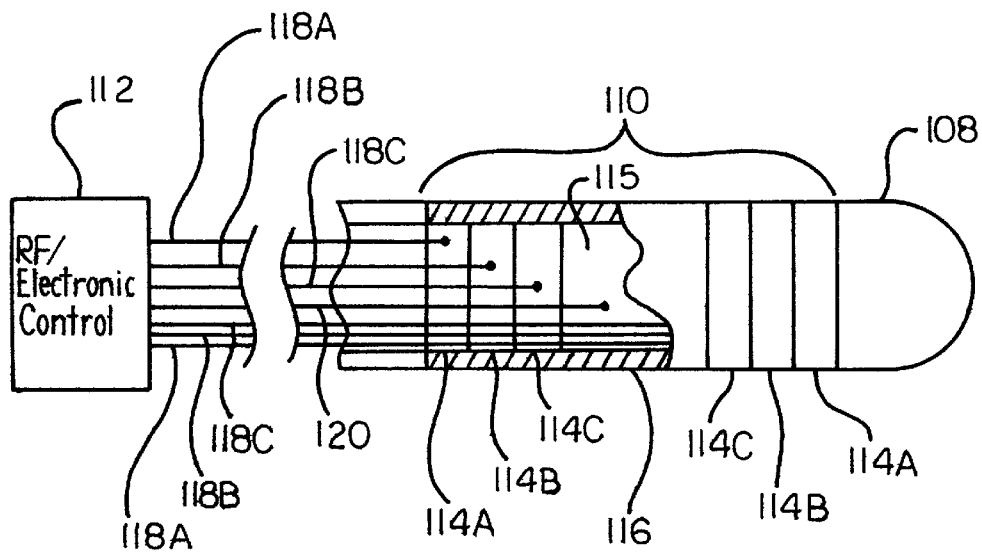
FIG. 15
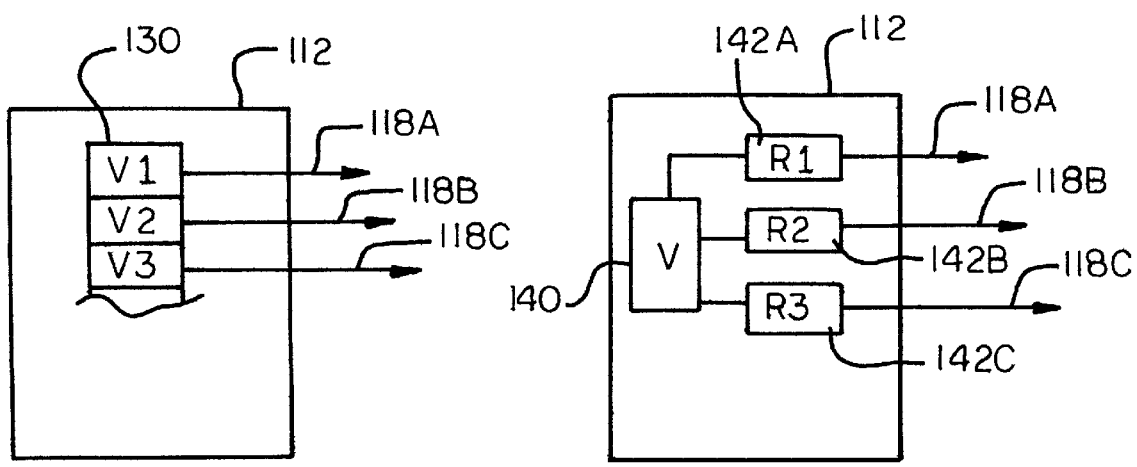
FIG. 16
FIG. 17

EVEN TEMPERATURE LINEAR LESION ABLATION CATHETER

CROSS-REFERENCE TO RELATED APPLICATION

The subject matter of this application is related to the subject matter of provisional patent application Ser. No. 60/090,209, filed Jun. 22, 1998, which is incorporated herein by reference and priority to which is claimed under 35 U.S.C. §119(e).

BACKGROUND OF THE INVENTION

1. Field of the Invention

The present invention relates to ablation catheters. In particular, the present invention relates to a linear lesion ablation catheter for producing a generally even temperature profile along the length of the catheter.

2. Description of Related Art

Ablation catheters are well recognized and important tools for conveying an electrical stimulus to selected locations within the human body. Ablation catheters have been used for many years for the treatment of certain types of cardiac arrhythmia. For example, ablation catheters have been used to interrupt or modify existing conduction pathways associated with arrhythmias within the heart. Ablation procedures also are used for the treatment of atrial ventricular (AV) nodal re-entrant tachycardia. Accepted treatments of this condition include ablation of the fast or slow AV nodal pathways. Known cardiac ablation procedures focus on the formation of lesions within the chambers of the heart at selected locations which will either prevent the passage of electrical signals associated with atrial premature contractions or prevent the formation of improper electrical pathways within the heart which can result in atrial arrhythmia.

Radio frequency (RF) catheter ablation has become increasingly popular for many symptomatic arrhythmias such as AV nodal re-entrant tachycardia, AV reciprocating tachycardia, idiopathic ventricular tachycardia, and primary atrial tachycardias. Nath, S., et al., "Basic Aspects Of Radio Frequency Catheter Ablation," *J Cardiovasc Electrophysiol*, Vol. 5, pgs. 863–876, October 1994. RF ablation is also a common technique for treating disorders of the endometrium and other body tissues including the brain.

A typical RF ablation system in its most basic form comprises an RF generator which feeds current to a catheter containing a conductive electrode for contacting targeted tissue. The system is completed by a return path to the RF generator, provided through the patient and a large conductive plate, which is in contact with the patient's back.

The standard RF generator used in catheter ablation produces an unmodulated sine wave alternating current at frequencies of approximately 500 to 1000 kHz. The RF energy is typically delivered into the patient between the electrode of the catheter and the large conductive plate in contact with the patient's back. During the delivery of the RF energy, alternating electrical current traverses from the electrode through the intervening tissue to the back plate. The passage of current through the tissue results in electromagnetic heating. Heating tissue to temperatures above 50° C. is required to cause irreversible myocardial tissue injury. However, heating tissue to temperatures above approximately 100° C. at the electrode/tissue interface can result in boiling of plasma and adherence of denatured plasma proteins to the ablation electrode. The formation of this coagulum on the electrode causes a rapid rise in electrical impedance and a fall in the thermal conductivity, resulting in loss of effective myocardial heating. Nath, S., et al., "Basic Aspects Of Radio Frequency Catheter Ablation," *J Cardiovasc Electrophysiol*, Vol. 5, pgs. 863–876, October 1994. Moreover, such extreme heating of the tissues can damage healthy tissue surrounding the targeted lesion.

Ablation catheters for burning lines in tissue are known. Examples of ablation catheters capable of forming linear lesions are shown in U.S. Pat. No. 5,720,775 to Larnard; U.S. Pat. No. 5,528,609 to Swanson; U.S. Pat. No. 5,549,661 to Kordis; U.S. Pat. No. 5,545,193 to Fleischmann; and U.S. Pat. No. 5,575,810 to Swanson. In these known linear ablation catheters, the current density of the linear conductive electrode portion is typically relatively stable in the center of the conductive electrode and tends to approach infinity at the ends of the conductive electrode. These areas of high current density lead to "edge effects" which can cause blood coagulation in these regions, which as stated above, causes a rapid rise in electrical impedance and a fall in the thermal conductivity resulting in a loss of effective myocardial heating. "Edge effects" also can cause extreme heating in the edge areas which can cause undesired tissue damage to healthy tissue surrounding the target tissue.

SUMMARY OF THE INVENTION

A linear lesion ablation catheter and method of the present invention includes a conductive ablating portion having a predetermined resistivity profile and/or voltage potential pattern for ablating tissue in a generally even temperature profile. In one embodiment, the conductive ablating portion is disposed on a distal portion of an elongate flexible member and has a resistance that increases exponentially along a portion of its length from a center of the ablating portion to a non-infinite value at opposite ends of the ablating portion. The ablating portion is adapted to produce a generally even temperature profile along a length of its surface when the ablating portion is in contact with a target tissue within a patient's body and an electrical ablating signal is applied to the ablating portion.

In one embodiment, the conductive ablating portion comprises a plurality of electrically connected conductive regions which extend from the center to the opposite ends of the ablating portion. In an even more specific embodiment, each of the conductive regions has a resistance value wherein the resistance values increase from section to section in successive orders of magnitude from the center of the ablating portion to the opposite ends of the ablating portion exponentially up to a non-infinite value.

The predetermined resistivity profile produces linear lesions on target tissue without the resulting "edge effects" or "hot spots" at the ends of the electrode common in prior art linear lesion ablation catheters.

BRIEF DESCRIPTION OF THE DRAWINGS

FIG. 15 is a schematic drawing of a generally even temperature linear lesion ablation catheter according to the present invention with a portion broken away and a portion in section.

FIG. 16 is a schematic drawing of an RF generator control unit of a linear lesion catheter of the present invention.

FIG. 17 is a schematic drawing of an RF generator control unit of a linear lesion catheter of the present invention.

DETAILED DESCRIPTION OF THE PREFERRED EMBODIMENT

Figure 1:
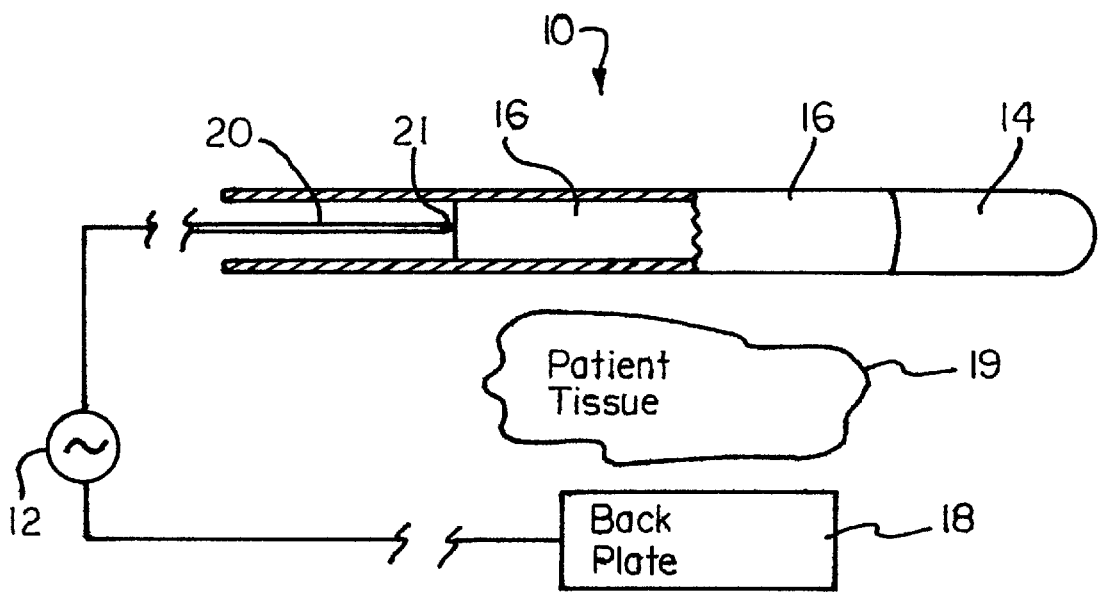
FIG. 1 is a schematic drawing of a known basic linear lesion ablation catheter system.

The present invention is directed to a linear lesion ablation catheter. As previously stated, ablation catheters are well recognized and important tools for conveying an electrical stimulus to selected locations within the human body. One such type of ablation catheter is a linear lesion ablation catheter. Linear lesion catheters are well known in the art for conveniently burning lines in tissue. FIG. 1 illustrates a schematic drawing of a basic RF linear lesion ablation catheter system 10.

System 10 includes an RF signal generator 12, a catheter body 14, an electrode 16, and a back plate 18. An electrical conductor 20 within catheter body 14 extends between, and electrically connects, electrode 16 to RF generator 12. As can be seen in FIG. 1, conductor 20 is electrically connected to electrode 16 at a junction 21 which is at a proximal end of electrode 16. In operation, RF generator 12 feeds a current to electrode 16 via conductor 20. During the delivery of RF energy, alternating electrical current traverses from electrode 16 through intervening tissue 19 of the patient to back plate 18. The passage of current through the tissue results in resistive (joule) heating.

When using an ablation system, the targeted tissue must be heated at temperatures above approximately 50° C. for effective ablation. However, temperatures at and above approximately 100° C. at the electrode/tissue interface can result in boiling of plasma and adherence of denatured plasma proteins to the ablation electrode. The formation of coagulum on the electrode causes a rapid rise in electrical impedance and a fall in the thermal conductivity resulting in loss of effective myocardial heating.

Figure 2:
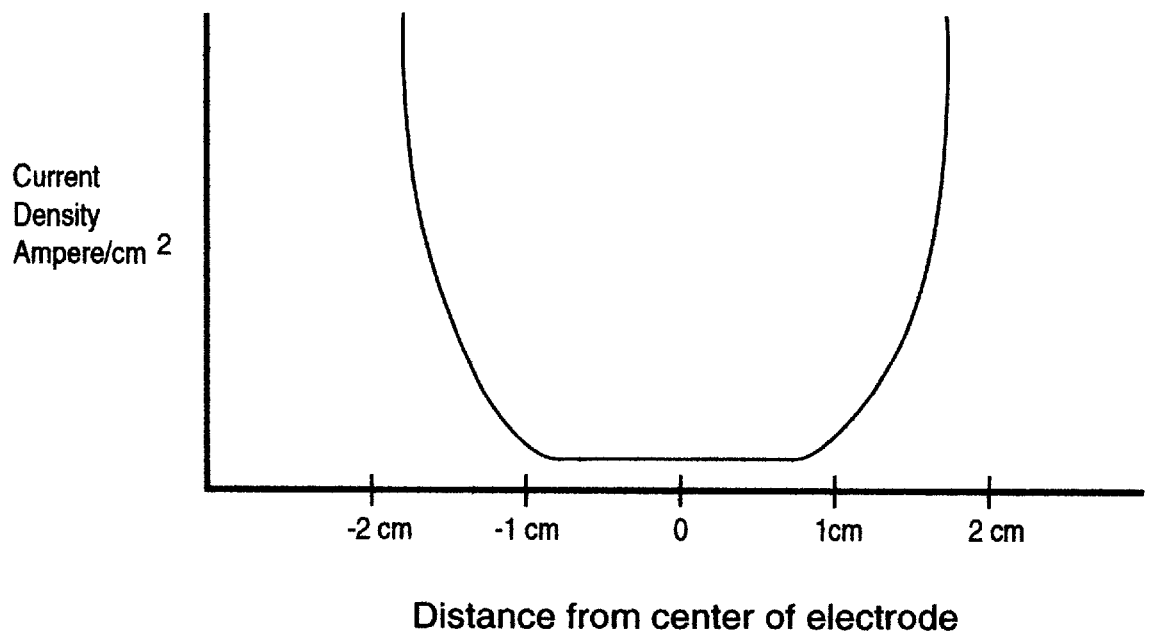
FIG. 2 is a current density plot of a known linear lesion ablation catheter.

FIG. 2 illustrates one of the problems with known linear lesion ablation catheters, such as that shown in FIG. 1. In particular, FIG. 2 is a current density plot of a known linear lesion catheter. The current density plot of FIG. 2 is based on a four-centimeters-long electrode with the "X" axis being the distance from the center of the electrode and the "Y" axis being current density in amperes per square centimeter. As can be seen in FIG. 2, the current density is relatively stable in the center of the electrode but goes to infinity at the ends of the electrode. The infinite current densities at the edge of the electrode leads to "edge effects" or "hot spots" which may be well in excess of 100° C. and which can cause blood coagulation. It can also cause undesirable tissue damage to healthy tissue surrounding the targeted tissue.

Figure 3:
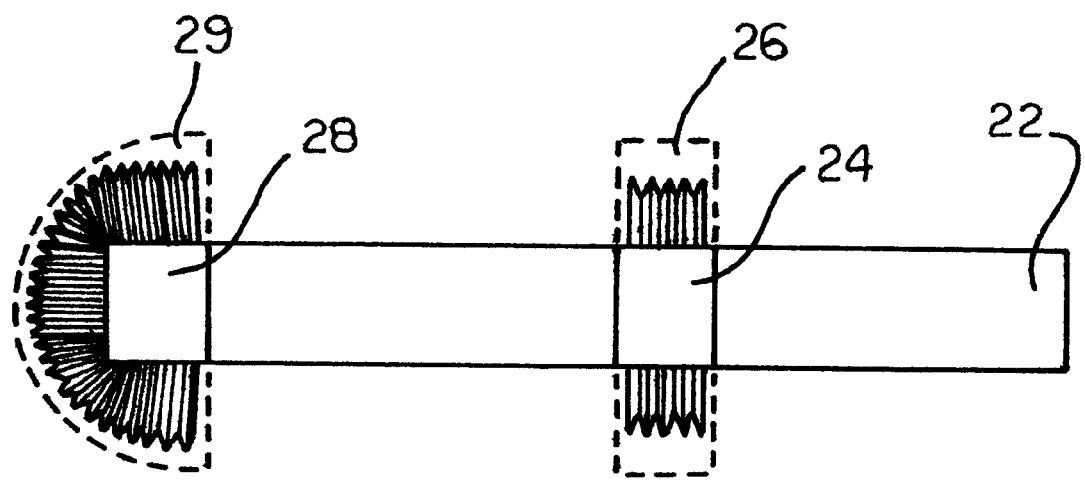
FIG. 3 is a schematic drawing illustrating current distribution at two points of an electrode in a linear lesion catheter.

FIG. 3 illustrates how the current density approaches infinity at the ends of the electrode. FIG. 3 depicts a simplified current distribution from two portions of an electrode 22 wherein the arrows illustrate current flow. A first portion 24 of electrode 22 feeds current to a disk-shaped volume 26 of tissue and blood surrounding electrode 22. A second portion 28 of electrode 22 feeds current to a much larger hemispherical shaped volume 29 of tissue and blood surrounding an end of electrode 22. Accordingly, a greater demand for more current exists at electrode portion 28 than at electrode portion 24, which causes the current density to head towards infinity at electrode portion 28. This extremely high current density at the ends of electrode 22 comprise the "edge effects" which produces the undesirable "hot spots," i.e., greatly elevated temperatures which denature more tissue than desired and cause undesirable blood coagulation.

A linear lesion ablation catheter of the present invention includes an ablating surface with a predetermined resistivity profile for developing current densities at the ends of the electrode in a controlled manner, thereby producing a generally even temperature profile without "hot spots" or "edge effects."

Figure 4:
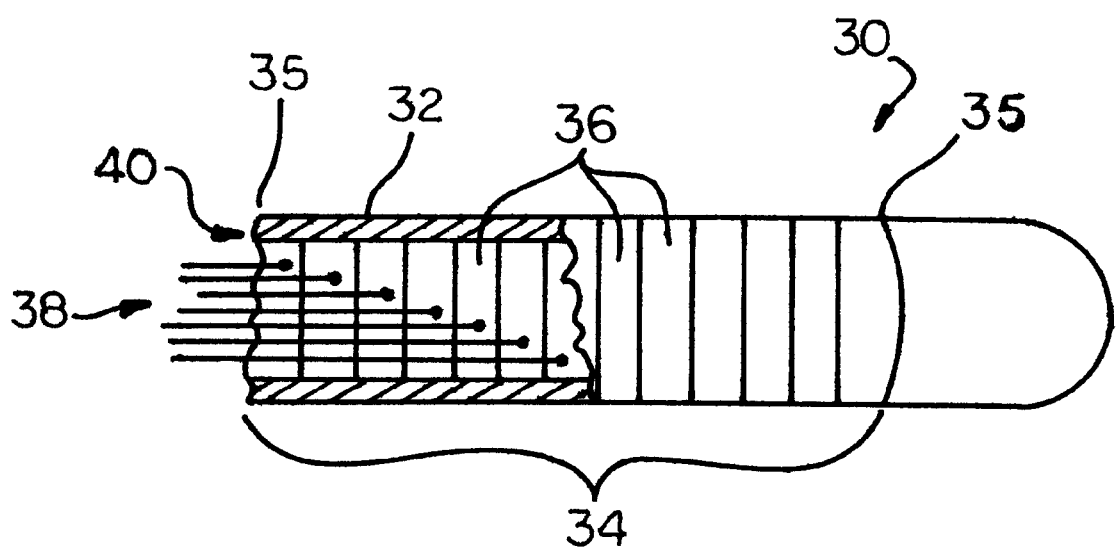
FIG. 4 is a schematic drawing of a generally even temperature linear lesion ablation catheter according to the present invention with a portion broken away and a portion in section.

FIG. 4 illustrates a linear lesion ablation catheter 30 of the present invention having a catheter body 32 and a conductive electrode portion 34 with ends 35. Electrode portion 34 comprises a series of conductive rings 36. Each ring 36 is connected to a corresponding electrical connector 38, which all extend from a proximal end 40 of catheter 30, and are connectable to one or more external power sources (not shown). Each ring 36 is either connected to its own external power source, or all of the rings are connected to a single power source providing a single power level to multiple rings or providing multiple outputs to provide a different power level for each ring. Moreover, each conductive ring 36 has a predetermined resistivity so that a combination of rings 36 can be arranged in series, with rings 36 having the same resistivity throughout a length of electrode portion 34 or each ring 36 having a different resistivity than other rings 36 to establish a desired predetermined resistivity profile. For example, in one embodiment, rings 36 closest to the center of the electrode portion 34 preferably have little to no resistivity while rings 36 adjacent ends 35 preferably have a much higher resistivity to counteract the tendency toward infinite current densities at ends 35. Finally, electrode portion 34 can include anywhere from two rings up to 10 or more rings, as necessary, to implement a desired predetermined resistivity profile and/or voltage potential pattern. In one embodiment, electrode portion 34 is about four centimeters long with a one-millimeter diameter.

A specific, predetermined resistivity profile for producing a generally even temperature profile (that can be accomplished with rings 36 or another structure) will be discussed further below.

Safe and effective linear lesion ablation generally occurs at current densities of about one ampere per square centimeter. Effective linear lesion ablation also may occur at lesser current densities, on the order of 0.5 to 0.8 amperes per square centimeter. However, for the purposes of the present invention and for the ease of description, about one ampere per square centimeter has been chosen as the desired current density. In this embodiment, the current density can be maintained at about one ampere per square centimeter along a majority of the length of the electrode portion except for the ends of the electrode portion where the current density increases slightly.

Figure 5:
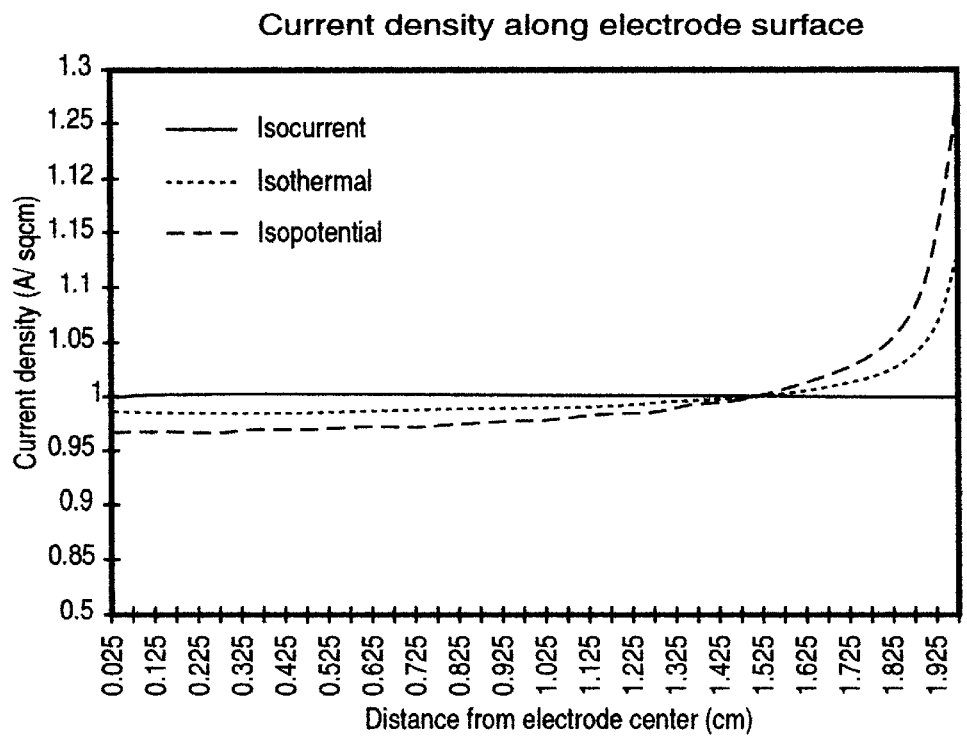
FIG. 5 is a graph illustrating a current density profile of a linear lesion ablation catheter according to the present invention.

FIG. 5 is a graph illustrating the current density along an electrode surface of a catheter of the present invention where the "X" axis represents a distance from the center of the electrode in centimeters, and the "Y" axis represents a current density on the electrode surface as measured in amperes per square centimeter. The linear lesion catheter of the present invention, represented by FIG. 5 (and FIGS. 6 and 7), has an electrode portion having a length of about four centimeters and a diameter of about one millimeter. This catheter can have the structure shown in FIG. 4 or another structure described in greater detail below.

For comparison purposes, FIG. 5 shows the current density pattern for three situations including an even current density along the electrode surface (isocurrent), an even voltage potential along the electrode surface (isopotential), and an even temperature profile along the electrode surface (isothermal). Of particular interest, the isothermal line represents the current density pattern for a linear lesion ablation catheter of the present invention. For example, as illustrated in FIG. 5, the current density of the catheter electrode is generally 0.97 amperes per square centimeter from the center of the electrode to about 1.5 centimeters from the center of the electrode, at which point the current density approaches 1.0 amperes per square centimeter. Between the 1.5 centimeter location and 2.0 centimeters (e.g., at the end of the electrode), the current density increases in a damped exponential fashion from about 1.0 to 1.1 amperes per square centimeter. Further, at about 1.9 centimeters from the center of the electrode, the current density is about 1.05 amperes per square centimeter. This moderated current density pattern is accomplished by varying the voltage potential along the length of the electrode portion as illustrated in FIG. 6.

Figure 6:
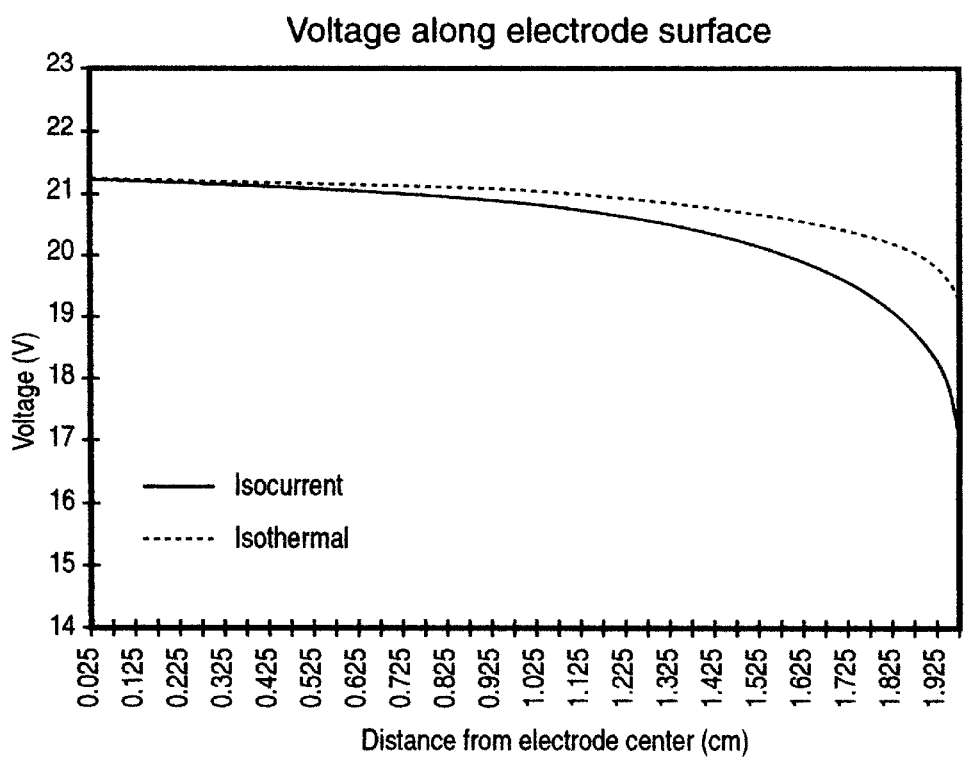
FIG. 6 is a graph illustrating a voltage potential profile of a linear lesion ablation catheter according to the present invention.

FIG. 6 is a graph illustrating the voltage potential pattern along the electrode ablating surface of a linear lesion catheter of the present invention where the "X" axis represents the distance from the center of the electrode in centimeters. The "Y" axis represents the voltage on the electrode surface as measured in volts. FIG. 6 shows the voltage potential for two situations including an even temperature profile along the electrode surface (isothermal) and an even current density pattern along the electrode surface (isocurrent).

As can be seen in FIG. 6, the voltage potential is approximately 21 volts at the center of the electrode portion and drops off to approximately 19 volts at the ends of the electrode portion. The voltage potential profile is, in turn, determined by the predetermined resistivity profile on the electrode portion, which is constructed by rings 36 of electrode 34 as in FIG. 4, or by another structure, as will be described in greater detail below. In addition, as described further below in connection with FIGS. 15 to 17, the voltage potential profile can be determined at an RF control unit.

Figure 7:
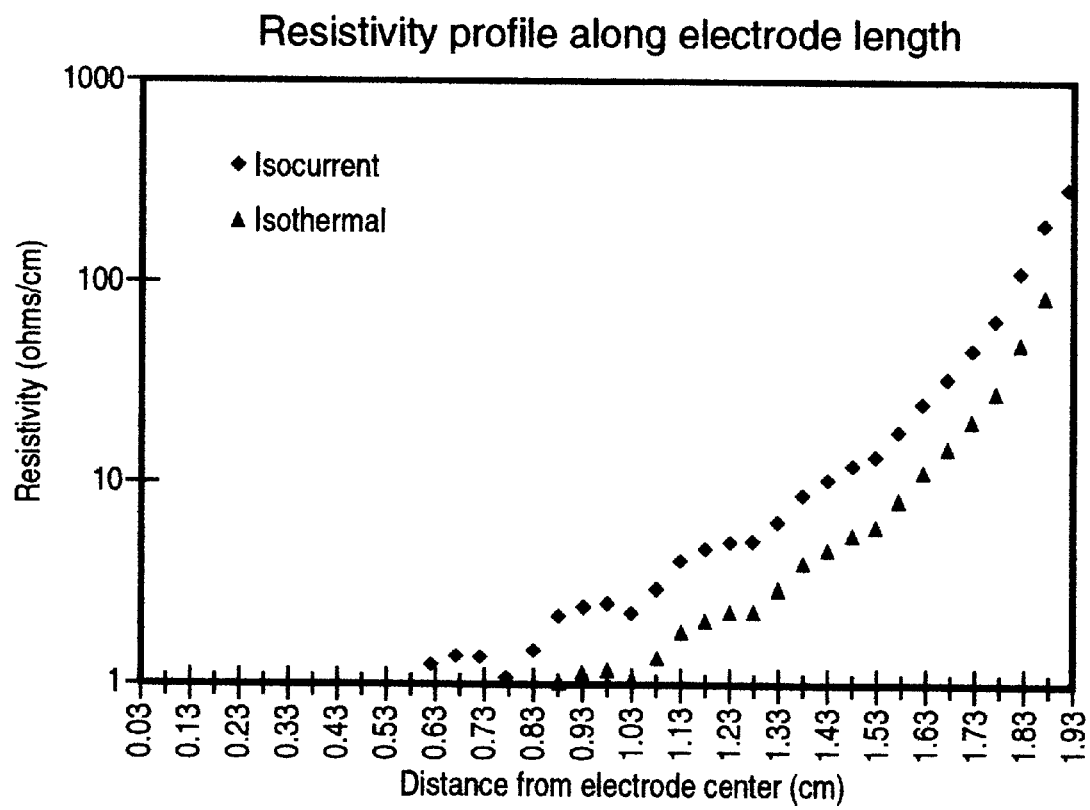
FIG. 7 is a graph illustrating a resistivity profile of a linear lesion ablation catheter according to the present invention.

FIG. 7 is a graph which illustrates the predetermined resistivity profile (resistance per unit length) in a linear lesion catheter of the present invention in order to achieve the desired current density (of FIG. 5) and voltage potential (of FIG. 6) needed for effective and safe linear lesion ablation. The "X" axis of FIG. 7 is the distance from the center of the electrode in centimeters taken along one direction from the center. For illustrative purposes, the "X" axis represents the electrode only from its center to one end, which is a distance of about two centimeters. The "Y" axis represents resistivity in ohms per centimeter. FIG. 7 shows the resistivity profile (per unit length) required to produce an even current density pattern (isocurrent) and a generally even temperature profile (isothermal). As seen in FIG. 7, the resistance in the first half centimeter from the electrode center is essentially zero ohms per centimeter of length, i.e., 0 to one ohm per centimeter. The resistance then begins to increase toward the ends of the catheter. The resistivity profile includes a resistance of about one to 10 ohms per centimeter from the 1.3 centimeter point to about 1.7 centimeters from the center, and about 10 to 100 ohms per centimeter from 1.7 centimeters to about two centimeters from the center (i.e., at the end of the electrode). In particular, the specific resistivity profile of FIG. 7 follows the distribution shown in Table 1 below, where D represents a distance from the center of the electrode, $Z_c$ represents a resistance of the electrode at a particular distance (D) from a center of the electrode for an even current density pattern, and $Z_t$ represents a resistance of the electrode at a particular distance (D) from a center of the electrode for an even temperature profile.

TABLE 1

| D (cm) | Isocurrent ($Z_c$) | Isothermal ($Z_t$) |
| --- | --- | --- |
| 0.025 | 0.08 | 0.04 |
| 0.125 | 0.31 | 0.14 |
| 0.225 | 0.33 | 0.15 |
| 0.325 | 0.27 | 0.12 |
| 0.425 | 0.78 | 0.36 |
| 0.525 | 0.43 | 0.20 |
| 0.625 | 1.24 | 0.57 |
| 0.725 | 1.36 | 0.62 |
| 0.825 | 1.48 | 0.68 |
| 0.925 | 2.43 | 1.11 |
| 1.025 | 2.28 | 1.03 |
| 1.125 | 4.02 | 1.82 |
| 1.225 | 5.02 | 2.27 |
| 1.325 | 6.40 | 2.89 |
| 1.425 | 10.1 | 4.55 |
| 1.525 | 13.5 | 6.00 |
| 1.575 | 18.1 | 8.06 |
| 1.625 | 25.2 | 11.1 |
| 1.675 | 33.2 | 14.6 |
| 1.725 | 46.0 | 20.2 |
| 1.775 | 65.2 | 28.4 |
| 1.825 | 114 | 49.3 |
| 1.875 | 200 | 85.0 |
| 1.925 | 739 | 309 |

Figure 8:
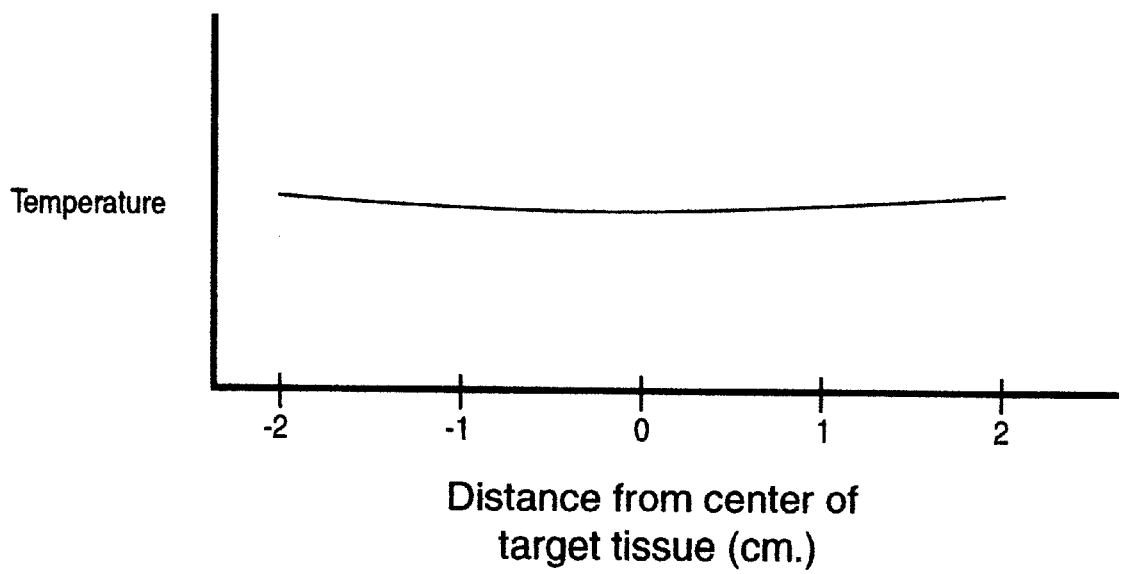
FIG. 8 is a graph illustrating a temperature profile of the target tissue during ablation by a catheter according to the present invention.

As stated above, the present invention provides a linear lesion ablation catheter having a generally even temperature profile along the length of the catheter to eliminate "hot spots." FIG. 8 illustrates a generally even temperature profile of a linear lesion catheter of the present invention. The "X" axis of FIG. 8 represents the distance from the center of the target tissue along the electrode surface in centimeters, and the "Y" axis represents temperature. The predetermined resistivity profile, and accompanying current density pattern, are selected according to the present invention to rise exponentially adjacent the ends of the electrode portion to compensate for a junction of a termination of the conductive ablating surface and the larger hemispherical volume of tissue disposed at the ends of the electrode. However, the exponential increase in resistance and current density are accomplished without approaching infinity asymptotically. This limited exponential pattern avoids "edge effects" at the ends of the electrode, as would occur if the resistance and current density increased too rapidly, i.e., infinitely, at the ends.

Moreover, a linear lesion ablation catheter of the present invention is not limited to the dimensions discussed above (e.g., four centimeters in length, one-millimeter diameter) nor to the specific resistivity profile of FIG. 7 and Table 1 (and accompanying current density and voltage potentials of FIGS. 5 and 6). Rather, catheters having larger or smaller dimensions (with corresponding longer, shorter, thicker and/or thinner electrode portions) will require slightly different resistivity profiles (and accompanying different current density and voltage potential patterns) to achieve a generally even temperature ablation profile. In addition, differing tissue types and vascularities also may require fine adjustments to the predetermined resistivity profile, all falling within the scope of the present invention.

Figure 9:
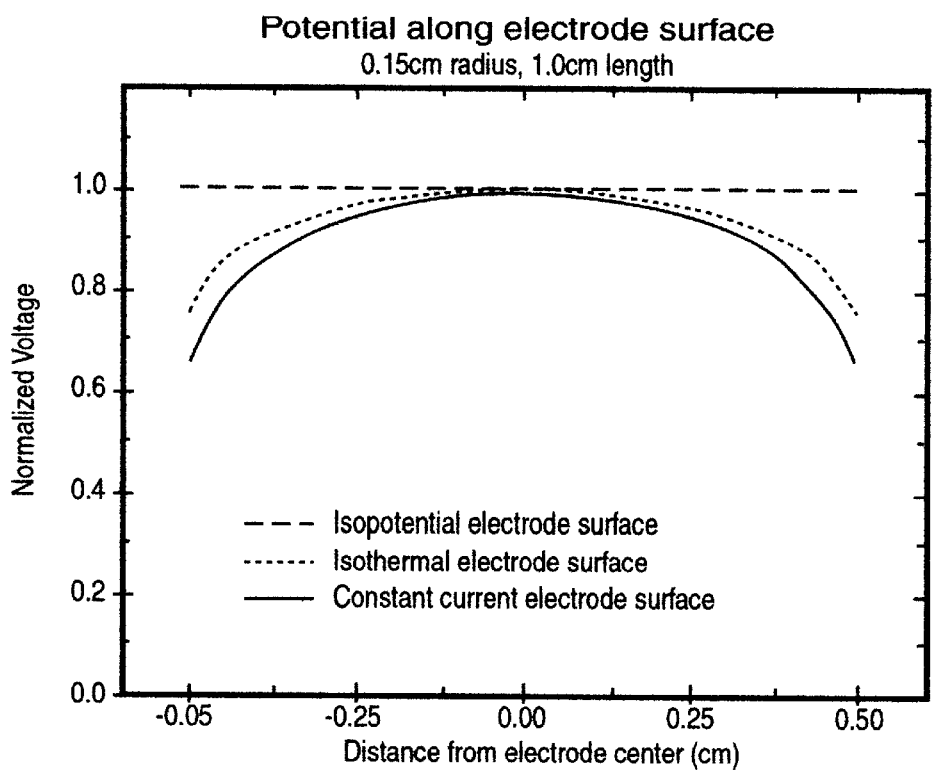
FIG. 9 is a graph illustrating a voltage potential profile of a linear lesion ablation catheter according to the present invention.
Figure 10:
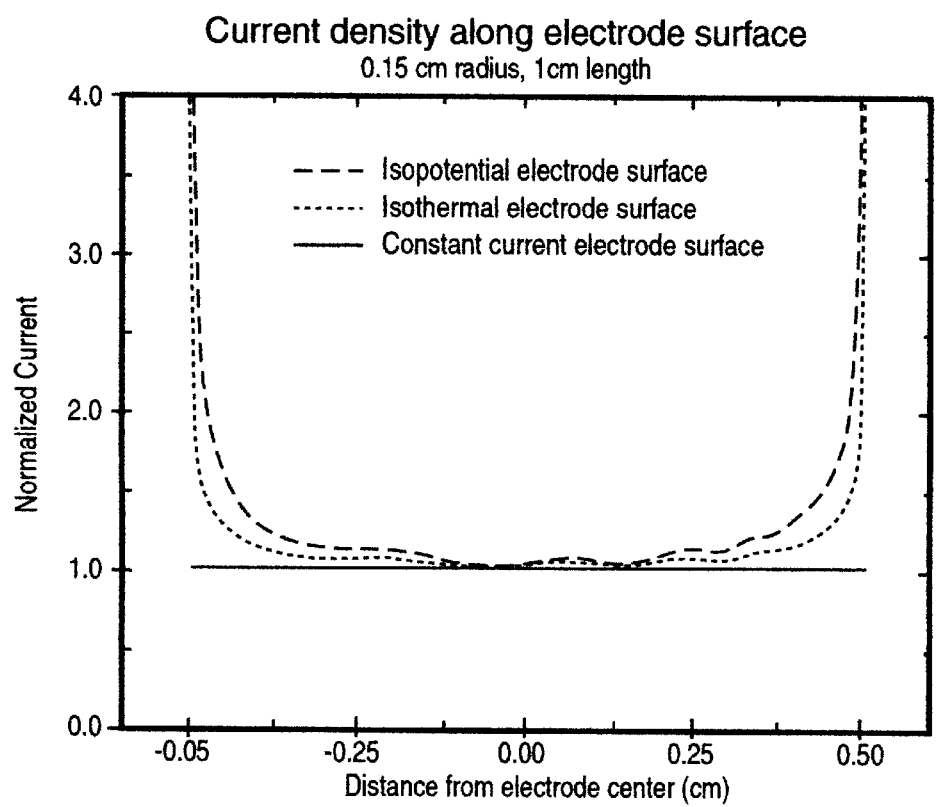
FIG. 10 is a graph illustrating a current density profile of a linear lesion ablation catheter according to the present invention.
Figure 11:
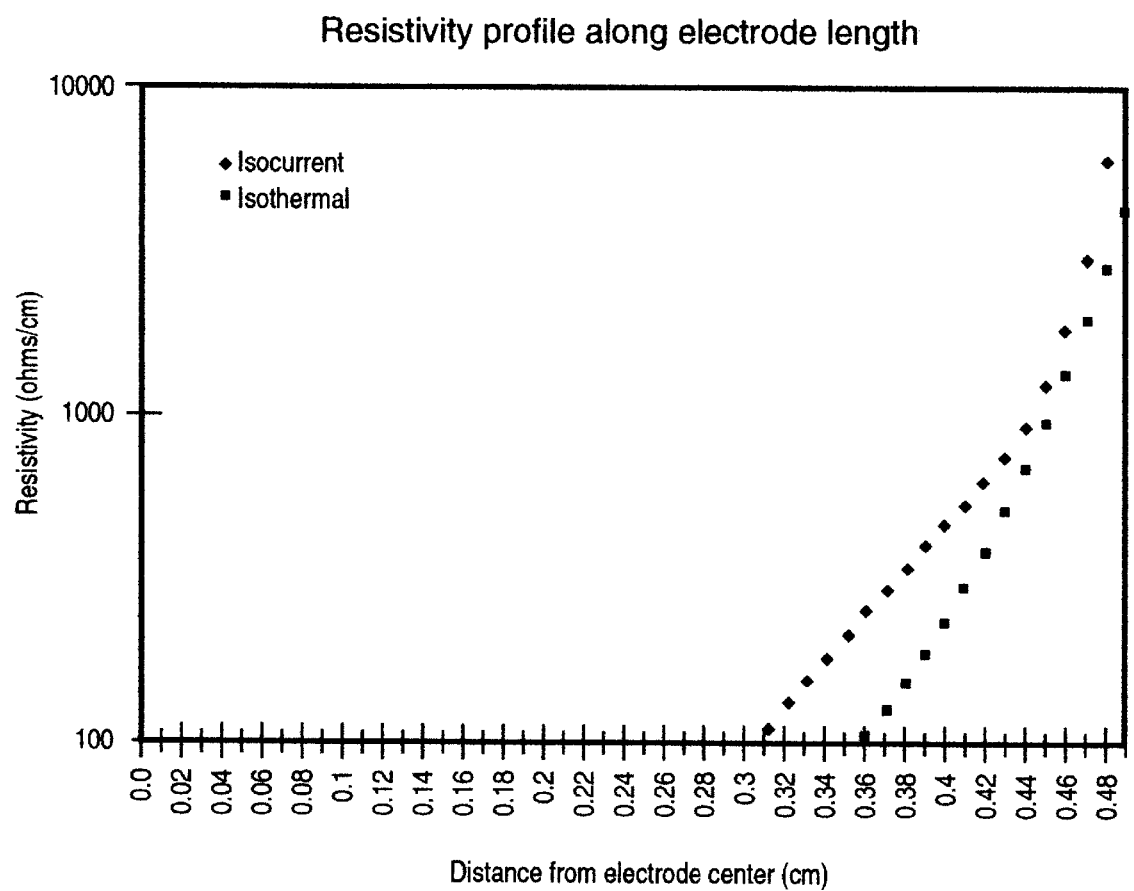
FIG. 11 is a graph illustrating a resistivity profile of a linear lesion ablation catheter according to the present invention.

For example, a shorter but thicker linear lesion ablation catheter of the present invention, can have an electrode surface with a length of 1.0 centimeters and a diameter of three millimeters. This shorter, thicker catheter produces a voltage potential as shown in FIG. 9 and a current density pattern as shown in FIG. 10. FIGS. 9 and 10 are graphs corresponding generally to the type of graphs of FIGS. 5 and 6 (as described above) except being applicable for the shorter, thicker catheter and showing the respective current density and voltage potential in both directions from the center of the electrode. FIG. 11 is a graph which illustrates the predetermined resistivity profile (resistance per unit length) in a shorter, thicker linear lesion catheter of the present invention in order to achieve the desired current density (of FIG. 10) and voltage potential (of FIG. 9) needed for effective and safe linear lesion ablation. In this embodiment, the "X" axis represents the electrode only from its center to one end, which is a distance of about 0.5 centimeters. FIG. 11 shows the resistivity profile (per unit length) required to produce an even current density pattern (isocurrent) and a generally even temperature profile (isothermal). As seen in FIG. 11, the resistance from a midpoint (center) of the electrode to a point 0.35 centimeters from the electrode center is generally 50 ohms per centimeter. The resistance then begins to increase toward the ends of the catheter. The resistivity profile includes a resistance of about 250 ohms per centimeter from the 0.35 centimeter point to about 0.45 centimeters from the center of the electrode, and about 1250 ohms per centimeter from 0.45 centimeters to about 0.5 centimeters (i.e., at the end of the electrode) from the center of the electrode. In particular, the specific resistivity profile of FIG. 11 follows the distribution shown in Table 2 below, where D represents a distance from the center of the electrode, $Z_c$ represents a resistance (ohms) of the electrode at a particular distance (D) from a center of the electrode for an even current density pattern, and $Z_t$ represents a resistance (ohms) of the electrode at a particular distance (D) from a center of the electrode for an even temperature profile.

TABLE 2

| D (cm) | Isocurrent ($Z_c$) | Isothermal ($Z_t$) |
| --- | --- | --- |
| 0 | 21 | 23 |
| 0.02 | 21 | 23 |
| 0.04 | 21 | 23 |
| 0.06 | 21 | 23 |
| 0.08 | 21 | 23 |
| 0.10 | 21 | 23 |
| 0.12 | 22 | 24 |
| 0.14 | 23 | 24 |
| 0.16 | 24 | 25 |
| 0.18 | 26 | 25 |
| 0.20 | 30 | 27 |
| 0.22 | 35 | 29 |
| 0.24 | 42 | 31 |
| 0.26 | 53 | 35 |
| 0.28 | 70 | 40 |
| 0.30 | 94 | 48 |
| 0.32 | 130 | 60 |
| 0.34 | 181 | 78 |
| 0.36 | 251 | 106 |
| 0.38 | 341 | 153 |
| 0.40 | 457 | 235 |
| 0.42 | 621 | 387 |
| 0.44 | 925 | 689 |
| 0.46 | 1781 | 1333 |
| 0.48 | 5957 | 2829 |

This shorter, thicker dimension linear lesion ablation catheter (represented by FIGS. 9–11) generally enjoys the same features and attributes of the longer, thinner catheter represented by FIGS. 5 through 8.

The specific resistance values and dimensions of the long and short catheters of the present invention are merely examples. Even longer, shorter, thinner and/or thicker catheters, including catheters with dimensions and resistance values between the specific examples of the longer, thinner and the shorter, thicker catheters, fall within the scope of the invention. However, the catheters of the present invention produce generally even temperature ablation profiles since they have substantially the same features and attributes.

For example, some catheters of the present invention have a resistivity profile which generally is divided into three sections over its length from a center of the linear electrode to the end. Each section from the center to the end has a resistivity that increases by an order of magnitude without approaching infinity at the end of the electrode. For example, the longer, thinner catheter (represented by FIG. 7) has a first section (0 to 1.3 centimeters from the center) having a resistivity of 0 ohm/centimeters (e.g., 0 to 9) (a first order of magnitude), a second section (1.3 to 1.7 centimeters from the center) having a resistivity of about 10 ohm/centimeters (e.g., 10 up to 100) (a second order of magnitude), and a third section (1.9 to 2.0 centimeters from the center) of resistivity of 100 ohm/centimeters (e.g., 100 to 400) (a third order of magnitude).

Similarly, a shorter, thicker catheter of the present invention (FIG. 11) has a first section (0 to 0.35 centimeters from the center) having a resistivity of about 50 ohms/centimeters (a first order of magnitude), a second section (0.35 to 0.45 centimeters from the center) having a resistivity of about 250 ohms/centimeters (a second order of magnitude), and a third section (0.45 to 0.5 centimeters from the center) having a resistivity of about 1250 ohms/centimeters (a third order of magnitude).

The resistivity profile of FIGS. 7 and 11 also can be deployed more or fewer sections than three resistance sections from a center to the ends. Moreover, in preferred embodiments, each section has an increasing resistance value toward the end of the section with the resistance of the utmost end section increasing significantly adjacent the end without asymptotically approaching infinity. In another embodiment, the resistance of each section is uniform throughout its length, and the sections are arranged in series from a center of the electrode toward the ends of the electrode with each section having a resistance value greater than the preceding adjacent section closer to the center. In one example of this embodiment, each section in series has a resistance value of about one order of magnitude greater than the preceding adjacent section closer to the center. Finally, in another embodiment, the resistance from the center to about one-half the distance to the end remains at a relatively uniform and unchanging level that is about two orders of magnitude lower than the resistance at the end of the electrode.

The resistivity profiles of the catheters of the present invention avoid "edge effects" normally associated with prior art linear lesion ablation catheters by providing an increased resistivity at the ends of the catheter without asymptotically approaching an infinite resistance at the ends.

In addition to the embodiment of catheter 30 of FIG. 4, a linear lesion ablation catheter of the present invention, which exhibits the features and attributes of the catheter represented by FIGS. 5 through 8 and the accompanying discussion, or the FIGS. of 9 through 11 and the accompanying discussion, can be embodied in other catheter designs as shown and described in connection with FIGS. 12 through 14.

Figure 12:
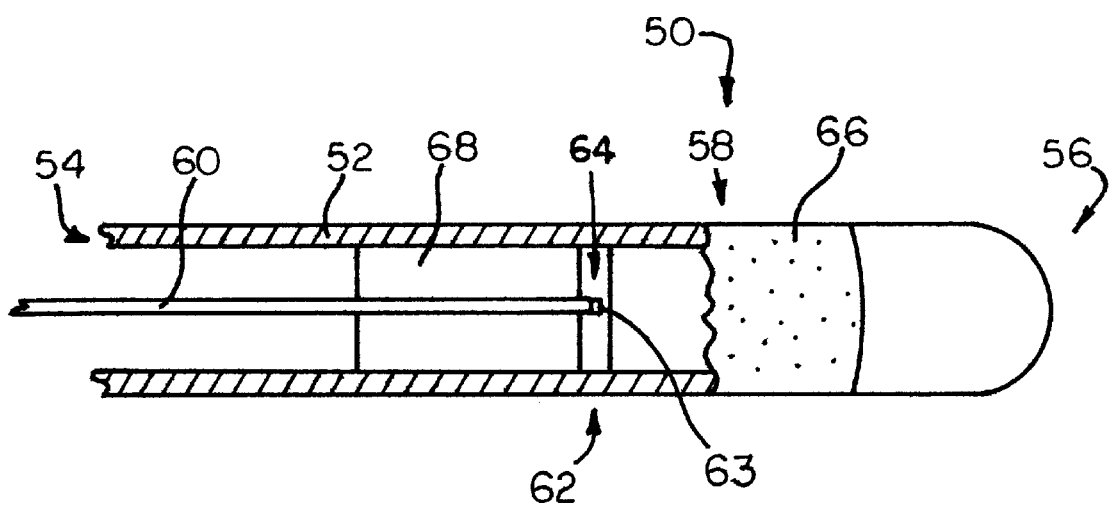
FIG. 12 is a schematic drawing of a generally even temperature linear lesion ablation catheter according to a preferred embodiment of the present invention with a portion broken away and a portion in section.

FIG. 12 is a schematic drawing with a portion cut away, of a generally even temperature linear lesion ablation catheter 50 according to one preferred embodiment of the present invention. Catheter 50 is used to implement the resistivity profile of FIG. 7 and/or the resistivity profile of FIG. 11 for a smaller dimension catheter. Catheter 50 includes a flexible catheter body 52 having a proximal end 54 and a distal end 56. Flexible catheter bodies are known to those skilled in the art. Catheter body 52 should be sufficiently pliable to permit the catheter to be advanced through the vascular system of the patient, for example, in to the heart and ultimately in to a pulmonary vein. In one embodiment of the present invention, distal end 56 of catheter body 52 may be pliable and less stiff than the remaining proximal portions of the catheter to assist the catheter in the advancement throughout the body. However, the pliability of catheter body 52 may also be consistent throughout its entire length. Additionally, catheter body 52 may be reinforced, for example, by use of a reinforcing braid or other such suitable strand material having high temporal strength.

Catheter 50 includes a conductive ablating surface, or electrode, 58 covering a portion of catheter body 52. As with catheter 30, in the preferred embodiment of the present invention, electrode 58 is four centimeters in length and has a diameter of one millimeter. Greater or lesser electrode lengths and greater or lesser diameters also may be used without departing from the spirit or scope of the present invention. For example, known linear lesion ablation catheters have typically been in the range of two to eight centimeters in length. With the present invention, electrodes as long as 12 centimeters are contemplated.

An electrical conductor 60 also is provided which extends from proximal end 54 to a substantially central region 62 of conductive surface 58. Conductor 60 is electrically connected to electrode 58 at junction 63 in a commonly known manner such as a weld, soldering or other mechanical connection. At proximal end 54, conductor 60 is adapted for connection to a power source (not shown). Typical power sources used in the ablation art are RF generators. Examples of known RF generators include the EPT-1000™ from E.P. Technologies, the EP-Shuttle™ manufactured by Stockert GmbH and the RFG-30™ from Radionics, Inc. These devices typically produce radio frequency signals in the 500 to 1000 kHz range power levels in the 0 to 100 watt range.

In the embodiment illustrated in FIG. 12, electrode 58 comprises a central conductive ring 64 and first and second deposited electrode regions 66 and 68, respectively, having increasing resistance toward the ends of the electrode region according to a predetermined resistivity profile as shown in FIG. 7, or FIG. 11. In the preferred embodiment, ring 64 is a metal conductive ring while first and second deposited electrode regions 66, 68 are thin film deposited material such as platinum or a conductive carbon. The deposited regions, 66, 68 are preferably applied by an ion process deposition. Ion deposition processes are known to those skilled in the art. Examples include the SPI-ARGENT™ and SPI-MET™ procedures from the Spire Corporation. These procedures are suitable for metalizing polymer surfaces, such as catheters, and can provide the desired thin film of metallic material as described above. Rastered ion beam processes are also known in the art. An example of a rastered ion beam process is the SPI-TEXT™ process from the Spire Corporation. In a rastered ion beam process, a suitable chemical is applied such that the metallic material is "pounded" and bonded into the polymer by being bombarded by the ion beam. This process results in a very thin, highly adherent metallic material film that is both mechanically and chemically bonded to the polymer.

Deposited regions 66 and 68 must be thin enough such that catheter 50 maintains its flexibility, while at the same time adhere to catheter body 52 during flexing without flaking off. By using a thin film deposition process, deposited regions 66, 68 enhance the mechanical tear and puncture resistance of catheter 50. Another benefit of using a thin film deposition process is that the thin material bonded to catheter body is thin enough that there is very little risk of "snagging" or "catching" during catheter delivery and use. In the preferred embodiment of the present invention, deposited regions 66, 68 are on the order of one to 10 microns thick.

Figure 13:
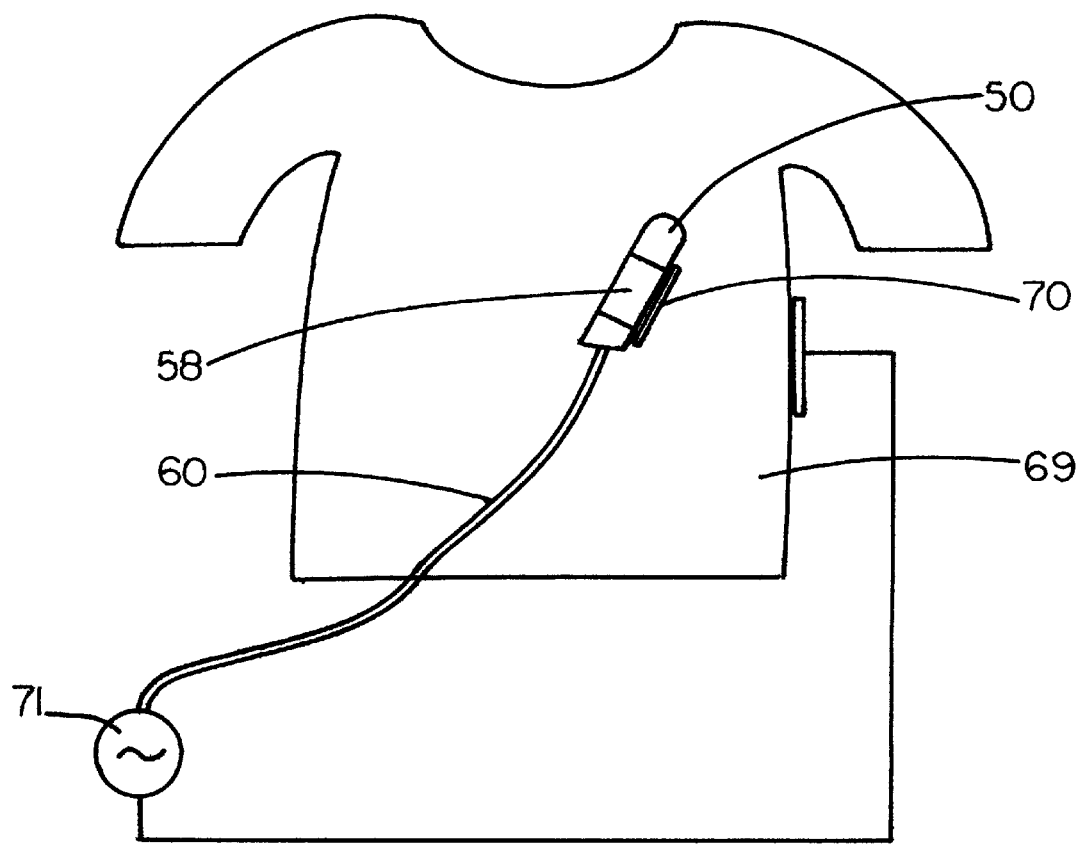
FIG. 13 illustrates a catheter according to the present invention in operation in a patient.

FIG. 13 illustrates catheter 50 in use. In operation, catheter 50 is positioned in a patient 69 such that electrode 58 is adjacent to an area of target tissue 70. Target tissue 70 may be in the heart, the endometrium, the brain or other placed of the patient where ablation is desired. Conductor 60 is connected to a power source 71 such as an RF generator. A back plate 72 also is provided which is positioned adjacent the body surface of patient 69 to provide a return path for the current to complete the electrical circuit. Current is then delivered to electrode 58 from RF generator 71. Because conductor 60 is connected to electrode 58 at the center of the electrode, and the resistivity of electrode 58 increases from the center towards the ends at a desired rate, as indicated in FIG. 7, the current density is substantially the same across a majority of the length of electrode 58 except for the ends of electrode 58. Because the current density is substantially the same across the entire length of electrode 58 and moderately increases at the ends, in a controlled fashion, the temperature profile at target tissue 70 is generally even during ablation as is illustrated graphically in FIG. 8. As previously stated, the temperature for effective ablation is typically between 50° and 100° C. The desired temperature may be determined by the operator and controlled, to some extent, by adjusting RF generator 71.

Figure 14:
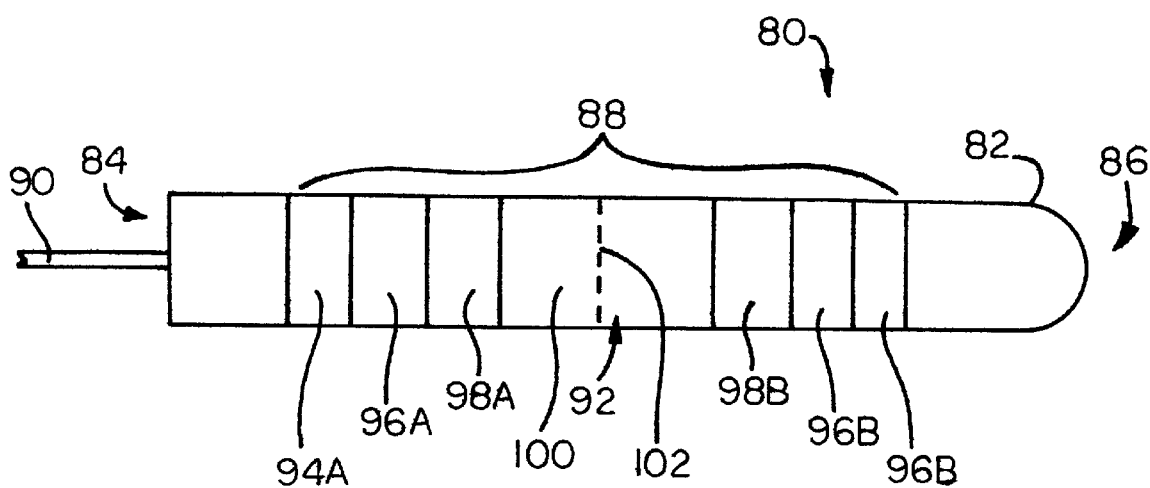
FIG. 14 is an alternative preferred embodiment of a generally even temperature linear lesion ablation catheter according to the present invention.

FIG. 14 illustrates an alternative preferred embodiment of the present invention for implementing a predetermined resistivity profile of FIG. 7 and the accompanying current density and voltage potential patterns. In particular, FIG. 14 is a schematic drawing of a generally even temperature linear lesion ablation catheter 80 of the present invention. Catheter 80 includes a catheter body 82 having a proximal end 84 and distal end 86. Catheter 80 also includes a conductive ablating surface 88 which covers a portion of catheter body 82. An electrical conductor 90 is also provided which extends from proximal end 84 to a substantially central region 92 of electrode 88. Conductor 90 is electrically connected to electrode 88 in a commonly known manner such as a weld, soldering or other mechanical connection. Electrode portion 88 is comprised of a number electrode sections, each with a different resistivity for accomplishing a predetermined resistivity profile to produce a generally even temperature ablation profile. As can be seen in FIG. 14, electrode portion 88 includes sections 94A and 94B, 96A and 96B, 98A and 98B, and section 100. Section 100 comprises a wire core having a very low resistance, on the order of 0.1 ohms per centimeter. In the embodiment illustrated, section 100 extends approximately one centimeter each direction of a center line 102 of electrode portion 88.

Sections 98A and 98B are approximately 0.5 centimeters in width and are also comprised of a wire coil. In order to homogenize the resistance of sections 98A and 98B, the wire coil could be made of a higher resistance material or could be a thinner gauge wire to achieve a higher resistance per unit length. Another approach would be to use a more sparsely wound coil than that found in section 100 and then cover the coil with a resistance coating to smooth the current density over it. The resistivity of sections 98A and 98B is on the order of a gradually increasing one to six ohms per centimeter toward the ends of electrode portion 88.

Sections 96A and 96B cover the regions 1.5 to 1.75 centimeters on each side of center line 102 of electrode portion 88. In the preferred embodiment of the present invention, sections 96A and 96B are covered only with a resistive spray and have no underlying electrode coils. The resistivity of sections 96A and 96B is on the order of a gradually increasing six to 25 ohms per centimeter.

Finally, sections 94A and 94B which cover the regions 1.75 to two centimeters away from center line 102 are covered only with a high resistive coating. The resistivity of sections 94A and 94B is on the order of 25 to 100 ohms per centimeter. There are many ways to achieve a desired resistivity and that the descriptions above are only exemplary. There are numerous other ways to wind coils or to deposit film, such as that previously described, to achieve the desired resistivity that would also fall with the spirit or scope of the present invention. Finally, a substantially similar arrangement of resistance sections can be arranged to implement the resistivity profile of FIG. 11 for a shorter, thicker catheter of the present invention, with corresponding resistance values which differ from the catheter represented by FIG. 7.

Multiple embodiments of the linear lesion ablation catheter of the present invention have been illustrated in which the resistance along the electrode has been varied in a selective fashion to produce a selected voltage potential and current density pattern and accompanying generally even temperature ablation profile. However, the desired generally even temperature profile can be accomplished by maintaining a relatively uniform resistance along the length of the electrode and then controlling the voltage potential on the electrode via an electronics control unit. For example, a linear lesion ablation catheter 108 of the present invention is shown in FIG. 15 having an electrode 110 and RF generator control unit 112. Electrode 110 has three or more rings 114A–114C extending in each direction from a center ring 115. Each ring 114A–114C has the same low nominal resistance value (e.g., one ohm/centimeter). Each ring 114A–114C also is connected to its own conductor 118A–118C, respectively, which extends from each ring 114A–114C to RF generator control unit 112.

The RF signal is applied at different power levels for each ring 114A–114C separately through the individual conductors 118A–118C. For example, the RF signal is applied so that an outer edge ring 114A produces a first voltage (e.g., 19.5 volts), an intermediate ring 114B produces a second voltage (e.g., 20 volts), and an inner more central ring 114C produces a third voltage (e.g., 21 volts). This arrangement yields an electrode in which the voltages are reduced at the outer edges of the electrode to yield the generally even temperature ablation profile, as shown in FIG. 8.

Producing a different voltage potential at each ring can be accomplished in at least two ways. A first example is illustrated in FIG. 16 in which a voltage regulator 130 of RF control unit 112 produces multiple separate voltage outputs (e.g., V1, V2, V3, etc.). Each conductor 118A–118C (which is conducted to an electrode ring 114A–114C, respectively) is electrically connected to one of the voltage outputs (V1, V2, V3, etc.) of voltage regulator 130. This arrangement produces a voltage potential pattern along electrode 110 to produce a current density pattern and resistivity profile as shown in FIGS. 5 through 7 and/or FIGS. 9 through 11. Of course, voltage regulator 130 can include more than three different voltage outputs for accommodating as many separate electrode rings as necessary.

In a second example shown in FIG. 17, RF control unit 112 includes a voltage regulator 140 and multiple resistors 142A–142C (R1, R2, R3, etc.). Voltage regulator 140 produces a single voltage output level, which is provided to each resistor (142A–142C). Each resistor 142A–142C, in turn, is connected to conductors 118A–118C that extend from rings 114A–114C (see FIG. 15). Each resistor 142A–142C has a different resistance value selected to produce a selected voltage potential, current density, and resistivity profile along the electrode 112, in substantial accordance with the patterns and profiles illustrated in FIGS. 5 through 7 and 9 through 11.

A linear lesion ablation catheter of the present invention has considerable advantages. The catheter applies ablative RF energy over an electrode having a predetermined resistivity profile that increases significantly in a limited manner at the ends of the electrode. Alternatively, an RF generator control unit produces an equivalent voltage potential pattern. The catheter produces a generally even temperature ablation profile in the target tissue. This heating profile is achieved with a current density pattern which is relatively uniform over the length of the electrode but which increases exponentially at the ends of the catheter in a noninfinite manner. This select application of RF energy ablates tissue without the accompanying "edge effects" commonly associated with prior art linear lesion ablation catheters.

Although the present invention has been described with reference to preferred embodiments, workers skilled in the art will recognize that changes may be made in form and detail without departing from the spirit and scope of the invention.

What is claimed is:

1. An ablation catheter comprising:
   an elongate flexible member; and
   a conductive ablating surface on a distal portion of the member, the surface having a resistance that increases exponentially along its length from a center to a non-infinite value at opposite ends of the surface.

2. The device as in claim 1, and further comprising:
   an electrical conductor extending within the member and having proximal and distal ends, wherein the proximal end of the conductor is adapted for connection to an external power source and the distal end of the conductor is connected to the conductive ablating surface.

3. The device as in claim 2, wherein the electrical conductor comprises a single electrically conductive wire.

4. The device as in claim 2, wherein the electrical conductor comprises a plurality of electrically conductive wires.

5. The device as in claim 1, wherein the conductive ablating surface is adapted to produce a generally even temperature profile along a length of its surface when the surface is in contact with a target tissue within a patient's body and an electrical ablating signal is applied to the ablating surface.

6. The device as in claim 1, wherein the conductive ablating surface comprises a plurality of electrically connected conductive regions which extend from the center of the conductive ablating surface to a first and a second end of the conductive ablating surface.

7. The device as in claim 1, wherein the ablating surface defines at least three electrically conductive regions of resistance including a first region having a resistance with a value of a first order of magnitude, a second region having a resistance with a value of a second order of magnitude, and a third region having a resistance with a value of a third order of magnitude, with the first region disposed closest to the center of the ablating surface and the third region disposed closest to one end of the ablating surface.

8. The device as in claim 7, wherein the resistance value of the first region is about 0 ohms per centimeter, the resistance value of the second region is about 10 ohms per centimeter, and the resistance value of the third region is about 100 ohms per centimeter.

9. The device as in claim 8, wherein the ablating surface has length of about four centimeters and the first region has a length of about 1.3 centimeters that extends from the center of the ablating surface towards one of the ends of the surface, the second region has a length of about 0.4 centimeters that extends from first region toward the end of the ablating surface, and the third region has a length of about 0.3 centimeters that extends from the second region to the end of the ablating surface.

10. The device as in claim 7, wherein the resistance value of the first region is about 50 ohms per centimeter, the resistance value of the second region is about 250 ohms per centimeter, and the resistance value of the third region is about 1250 ohms per centimeter.

11. The device as in claim 10, wherein the ablating surface has length of about one centimeter and the first region has a length of about 0.35 centimeters that extends from the center of the ablating surface towards one of the ends of the surface, the second region has a length of about 0.10 centimeters that extends from first region toward the end of the ablating surface, and the third region has a length of about 0.05 centimeters that extends from the second region to the end of the ablating surface.

12. The device as in claim 7, wherein the first region has a length of about 65 to 70 percent of the length of the ablating surface that extends from the center of the ablating surface towards one of the ends of the surface, the second region has a length of about 20 percent of the length of the ablating surface that extends from the center toward the end of the surface, and the third region has a length of about 10 to 15 percent of the length of the ablating surface that extends from the center to the end of the surface.

13. A device for ablating tissue within a patient's body comprising:
   an elongate body; and
   a linear electrode attached to the body wherein the linear electrode has a midpoint and opposite ends, wherein a resistance of the linear electrode increases exponentially along a length of the electrode from the midpoint to a non-infinite value at the ends of the electrode.

14. The device as in claim 13, wherein the linear electrode is adapted to produce a generally even temperature profile along its length when in contact with a target tissue within a patient's body and an electrical ablating signal is applied to the linear electrode.

15. The device as in claim 13, wherein the temperature is substantially equal from the first end of the linear electrode to the second end of the electrode when power is supplied to the electrode.

16. The device as in claim 13, wherein the power source is external to the body.

17. The device as in claim 13, wherein the electrode comprises a plurality of electrically connected conductive regions.

18. The device as in claim 17, wherein the plurality of conductive regions extend from the midpoint portion of the electrode to the opposite ends of the electrode and wherein a value of the resistance of each of the plurality of conductive regions increases in successive orders of magnitude from the midpoint to the opposite ends of the electrode.

19. The device as in claim 13, wherein the electrode defines at least three electrically conductive regions of resistance including a first region having a resistance with a value of a first order of magnitude, a second region having a resistance with a value of a second order of magnitude, and a third region having a resistance with a value of a third order of magnitude, with the first region disposed closest to a midpoint of the electrode and the third region disposed closest to one end of the electrode.

20. The device as in claim 19, wherein the first region has a length of about 65 to 70 percent of the length of the electrode that extends from the midpoint of the electrode towards one of the ends of the electrode, the second region has a length of about 20 percent of the length of the electrode that extends from the midpoint toward the end of the electrode, and the third region has a length of about 10 to 15 percent the length of the electrode that extends from the midpoint to the end of the electrode.

21. The device as in claim 20, wherein the resistance value of the first region is about 0 ohms per centimeter, the resistance value of the second region is about 10 ohms per centimeter, and the resistance value of the third region is about 100 ohms per centimeter.

22. The device as in claim 20, wherein the resistance value of the first region is about 50 ohms per centimeter, the resistance value of the second region is about 250 ohms per centimeter, and the resistance value of the third region is about 1250 ohms per centimeter.

23. The device as in claim 13, and further comprising:
   an electrical conductor within the catheter body wherein the electrical conductor has proximal and distal ends and wherein the proximal end of the conductor is adapted for connection to a power source and the distal end of the conductor is connected to the linear electrode.

24. The device as in claim 23, wherein the electrical conductor is connected to a substantially central region of the electrode.

25. The device as in claim 23, wherein the electrical conductor comprises a single electrically conductive wire.

26. The device as in claim 23, wherein the electrical conductor comprises a plurality of electrically conductive wires.

27. The device as in claim 13, wherein the linear electrode has a first section with a generally uniform resistivity and a second section closer to the end with a resistivity that increases exponentially without approaching infinity at the ends.

28. The device as in claim 13 wherein the linear electrode has more than one section with each section having a constant resistivity throughout their length and the sections being arranged in series with each successive section beginning from the midpoint of the electrode toward the ends of the electrode having a resistance value that is one order of magnitude higher than the immediately adjacent section closer to the center of the electrode.

29. The device as an claim 28 wherein the linear electrode has at least three sections extending in each direction from the center of the electrode.

30. The device in claim 13 wherein the linear electrode has more than one section with each section having a resistivity that increases along their length and the sections being arranged in series with each successive section beginning from the midpoint of the electrode toward the ends of the electrode having a resistance value that is one order of magnitude higher than the immediately adjacent section closer to the midpoint of the electrode.

31. The device in claim 13 wherein the linear electrode has a first section having an constant resistivity and one or more sections having resistivity which increases along their length, with the sections arranged in series and the first section disposed closest to the midpoint of the electrode and having a resistance value that is at least one order of magnitude lower than the one or more sections having increasing resistivity.

32. A device for ablating tissue within a body comprising:
an elongate catheter; and
means for producing an ablating signal on a conductive distal surface of the catheter with the distal surface having a resistivity that increases exponentially to a non-infinite value along the length of the distal conductive ablating surface from a center of the surface to at least one end of the surface.

33. A method of ablating target tissue within a body, the method including the steps of:
positioning a linear electrode of a catheter in the body adjacent the target tissue; and
ablating the target tissue with the electrode at a generally uniform temperature along a length of the electrode,
wherein the ablating step further comprises:
applying an electrical ablating signal to the electrode over a resistance of the electrode that increases in value exponentially along a length of the electrode from a midpoint to a non-infinite value at the ends of the electrode.

34. The method of claim 33, wherein the applying step further comprises:
arranging at least three electrically conductive regions of resistance in series including a first region having a resistance with a value of a first order of magnitude, a second region having a resistance with a value of a second order of magnitude, and a third region having a resistance with a third order of magnitude, which further comprises disposing the first region closest to a center of the electrode and the third region disposed closest to one end of the electrode.

35. The method of claim 34, further comprising:
extending the first region over a length of about 65 to 70 percent of the length of the electrode that extends from the center of the electrode towards one of the ends of the electrode;
extending the second region over a length of about 20 percent of the length of the electrode that extends from midpoint toward the end of the electrode; and
extending the third region has a length of about 10 to 15 percent the length of the electrode that extends from the center to the end of the electrode.

36. The method of claim 35, wherein extending steps further comprise:
providing the first region with a resistance value of about 0 ohms per centimeter;
providing the second region with a resistance value of about 10 ohms per centimeter; and
providing the third region with a resistance value of about 100 ohms per centimeter.

37. The method of claim 35, wherein extending steps further comprise:
providing the first region with a resistance value of about 50 ohms per centimeter;
providing the second region with a resistance value of about 250 ohms per centimeter; and
providing the third region with a resistance value of about 1250 ohms per centimeter.

38. A method of producing a linear lesion along a target tissue comprising:
positioning a linear electrode in the body adjacent the target tissue; and
heating the target tissue with the electrode at a generally uniform temperature along the length of the electrode without necrosing healthy tissue surrounding the target tissue,
wherein the heating step further comprises:
applying an electrical ablating signal to the electrode over a resistance of the electrode that increases in value exponentially along a length of the electrode from a midpoint to a non-infinite value at the ends of the electrode.

39. An ablation catheter comprising:
an elongate flexible member;
an electrode disposed on a distal portion of the member and defining a plurality of electrically connected conductive regions which extend from the center of the electrode to a first end and a second end of the electrode with all of the conductive regions having substantially the same resistance value;
a plurality of conductors, each conductor having a distal end connected to one of the conductive regions of the electrode and extending through the elongate flexible member to a proximal portion of the member; and
an external control unit having multiple voltage outputs with each voltage output having a different value wherein each voltage output is connected to a proximal end of one of the conductors, wherein the conductive regions along the electrode produce a voltage pattern that decreases at the edges of the electrode.

40. An ablation catheter comprising:

an elongate flexible member;

an electrode disposed on a distal portion of the member and defining a plurality of electrically connected conductive regions which extend from the center of the electrode to a first end and a second end of the electrode;

a plurality of conductors, each conductor having a distal end connected to one of the conductive regions of the electrode and extending through the elongate flexible member to a proximal portion of the catheter; and an external control unit having a single voltage output connected to multiple resistors with each resistor having a different value, and each resistor being connected to a proximal end of one of the conductors.

* * * * *